United States Patent [19]

Grimsby et al.

[11] Patent Number: 4,620,912

[45] Date of Patent: Nov. 4, 1986

[54] PROCESS FOR THE PRODUCTION OF DICHLOROHYDRIN

[75] Inventors: F. Norman Grimsby; George C. Blytas, both of Houston, Tex.

[73] Assignee: Shell Oil Company, Houston, Tex.

[21] Appl. No.: 814,333

[22] Filed: Dec. 27, 1985

[51] Int. Cl.$^4$ ............................................. B01D 57/02
[52] U.S. Cl. ............................. 204/182.4; 204/182.3; 204/81
[58] Field of Search ............... 204/182.3, 182.4, 182.5, 204/81

[56] References Cited

U.S. PATENT DOCUMENTS 3,909,382  9/1975  Mueller et al. .................. 204/182.4

Primary Examiner—R. L. Andrews
Attorney, Agent, or Firm—Ronald R. Reper

[57] ABSTRACT

In a multistage reaction system for the preparation of dichlorohydrin by the reaction of allyl chloride, water and chlorine and where the hydrochloric acid by-product is removed by electrodialysis, increased efficiency for acid removal by electrodialysis results from at least partial neutralization of the acid in the electrodialysis concentrate receiving stream, enabling the use of smaller electrodialysis membrane area and or lower energy consumption.

6 Claims, 1 Drawing Figure

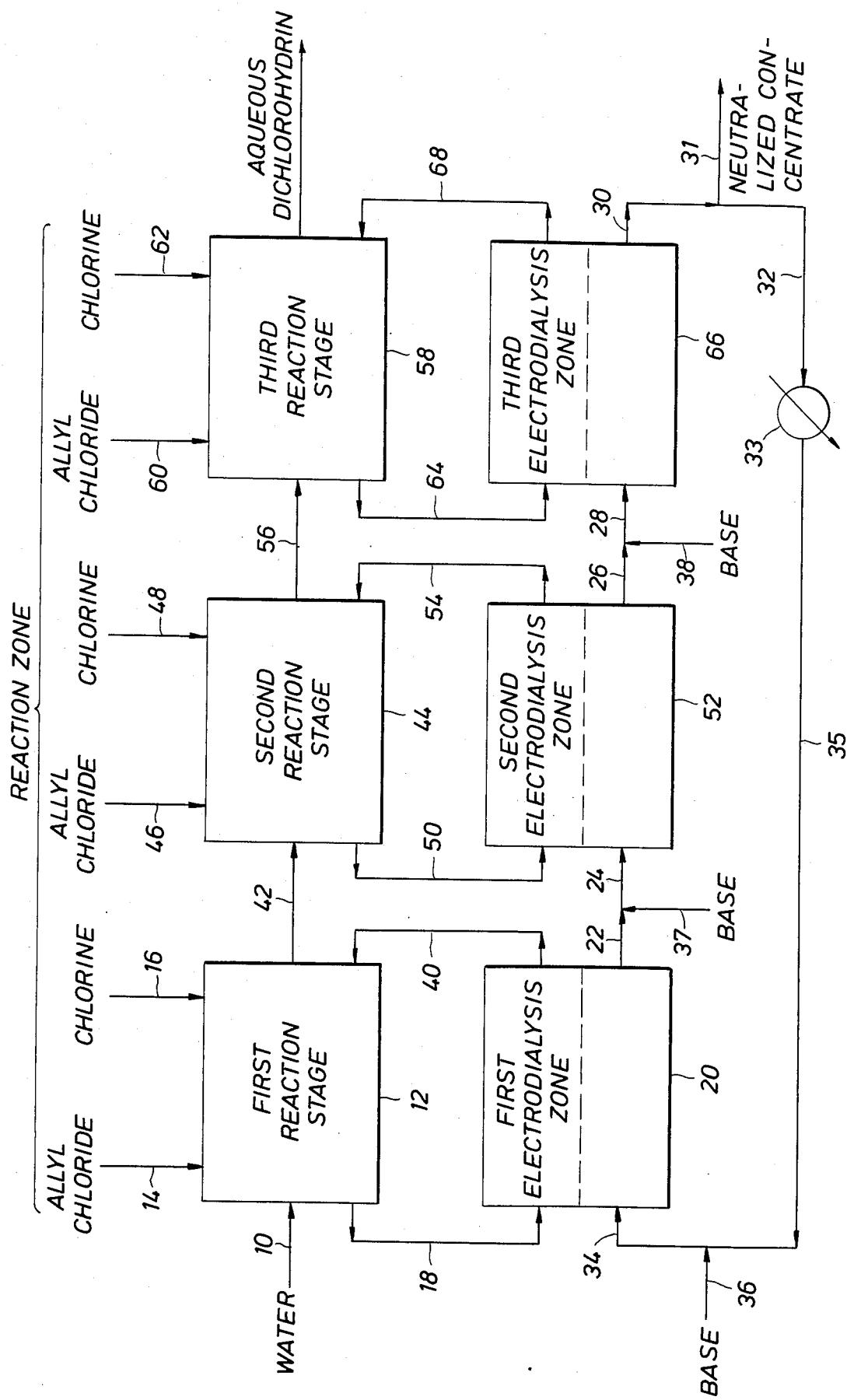

PROCESS FOR THE PRODUCTION OF DICHLOROHYDRIN

BACKGROUND OF THE INVENTION

It is known to prepare an aqueous solution of dichlorohydrin e.g., 2,3 dichloro-1-propanol and 1,3 dichloro-1-propanol, herein collectively dichlorohydrin, by reacting in a reaction zone allyl chloride, water and chlorine in dilute aqueous phase.

U.S. Pat. No. 2,714,121, incorporated herein by reference, discloses producing halohydrins by using high dilution of e.g. 250 to 400 volumes of water per volume of e.g., a halosubstituted hydrocarbon in aqueous medium with subsequent addition of the halogen, and keeping the organic by-product phase dispersed as fine particles.

U.S. Pat. No. 2,714,123, incorporated herein by reference, discloses producing an aqueous solution of dichlorohydrin in a series of reaction zones wherein substantially all of the water is fed to the first of the reaction zones and the other reactants added in substantially equimolar proportions into each of the other reaction zones.

U.S. Pat. No. 3,909,382 discloses recovering acid values, such as hydrochloric acid formed during olefin chlorohydrination, by series flow through a plurality of electrodialysis stages to upgrade the acid to higher concentration.

Japanese Pat. No. 74,00369 relates that the product mixture from the reaction of a lower olefin, chlorine and water can be electrodialyzed to remove the by-produce ions of hydrogen and chlorine, and the ion-depleted chlorohydrin solution circulated to the single reaction zone, enabling the production of a concentrated aqueous chlorohydrin solution.

As disclosed in copending application Ser. No. 814,331 (K-2317), filed Dec. 27, 1985, in a multistage dichlorohydrin production system, increased selectivity to the desired dichlorohydrin may be obtained by electrodialyzing the reaction effluent of one stage prior to being fed to a subsequent stage.

A disadvantage of e.g., the process in said copending application Ser. No. 814,331 (K-2317) filed Dec. 27, 1985 is that removal of the ions requires substantial electrodialysis membrane area, adding to the capital cost required to achieve the desired selectivity.

It has now been found that advantageous selectivity can be retained by employing an electrodialysis unit in parallel flow to at least one reaction stage to remove a substantial part of the acid from the reaction mixture into a concentrate stream, and neutralizing said acid in said concentrate stream.

SUMMARY OF THE INVENTION

According to the invention there is provided in a continuous process for the production of an aqueous solution of dichlorohydrin by the reaction of allyl chloride, water and chlorine in a reaction zone, the method for removing by-product hydrogen and chloride ions which comprises:

(a) electrodialyzing a significant part of the reaction mixture in an electodialysis zone to afford, (1) a concentrate stream having a chloride ion content higher than the concentrate inlet feed to said electrodialysis zone, and (2) a diluate stream containing dichlorohydrin and having a lower chloride content than said reaction mixture electrodialysis feed, (b) neutralizing a substantial portion of the hydrogen ions in the concentrate stream by the addition of a basic substance to said concentrate stream, and (c) withdrawing a portion of said neutralized concentrate stream, and (d) recylcing said diluate stream from said electrodialysis zone to said reaction zone.

THE DRAWING

The FIGURE depicts a schematic flow diagram of a preferred embodiment of the invention.

DESCRIPTION OF PREFERRED EMBODIMENTS

In the principal reaction, allyl chloride is converted to a mixture of the two isomers of dichloropropanol, by reaction with hypochlorous acid, HClO, which is readily formed when chlorine is dissolved in water. The dichlorohydrination reaction takes place readily at temperatures in the range from about 15° to about 55° C. Decreased temperature rapidly increases the amount of dissolved chlorine as well as the concentration of the hypochlorous acid. For maximum chlorohydrin yield it is necessary to run the reaction at low concentrations of chloride ion and of chlorohydrin, i.e., with high water dilution which reduces the formation fo undesired by-products e.g., trichloropropane and tetrachloropropyl ether.

The reaction zone effluent typically has a low pH, resulting from the hydrogen chloride formed as by-product resulting from the formation of the dichlorohydrin.

It is an advantage of the present invention that the electrodialysis is rendered more efficient by neutralization in the concentrate stream. By the addition of a basic material to the concentrate stream, back diffusion of the removed hydrogen ions into the diluate streams is substantially avoided, resulting in more efficient (more ion removal per unit of electrical power applied) electrodialysis of the reaction zone mixture.

Electrodialysis is by now a well established industrial process. Basically, an electrodialysis unit comprises a plurality of membranes alternatively anionic and cationic placed between an anode and a cathode connected to a direct current source. The membranes are usually separated from each other by 1 to 5 mm using appropriate spacers and the feed stream may be made to flow through a spacer creating a turbulent path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

If a feed stream is introduced uniformly from the top of the electrodialysis unit, it will be found that passages in the unit having an anion membrane of the cathode side of the passage and vice versa will become concentrated streams higher in ionized (herein saline) components and the other streams in passages bounded by anion membranes on the anode side and cathode membranes on the cathode side will become depleted in ionized components. Such depleted stream or streams are herein referred to as the diluate stream.

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volume of diluate/concentrate streams and membrane pore size.

The anionic and cationic membranes employed herein are known in the art. Generally, the anionic and cationic membranes comprise flat sheets of inorganic or organic materials which have extreme water-insolubility. Preferably the anionic and cationic membranes are prepared from synthetic organic resinous, polymeric materials, (e.g., polystrene polymers) to which are bonded ionic groups. Any strong or weak base (e.g., tertiary amines or quanternary ammonium compounds) can be chemically bonded to the organic material to form an ionic exchange membranes; and strong or weak acid (e.g., aryl sulfonates) can be chemically bonded to the organic resinous material to form cationic exchange membranes.

Generally, the anionic and cationic membranes herein, either in the form of laminate or a homogeneous cast or sheet, are "backed" or reinforced with an imbedded screen or matrix of synthetic reinforcing fabric, for example, fiberglass or dynel (tradename for modified acrylic polymers), to provide them with a substantially rigid structure. Other 'backings' can be used, provided the anionic and cationic membranes remain essentially impervious to mass flow but porous enough to permit ion migration or transfer.

The cation and anion-exchange membranes can be any cation- and anion-selective membranes respectively which are essentially stable in the feed water and not chemically degraded by the components therein. Exemplary membranes are disclosed in the article entitled "Electrodialysis", Kirk-Othmer, Encyclopedia of Science and Technology, pages 846–865 (Second Edition, Interscience Publishers, 1965) and U.S. Pat. Nos. 2,730,768, 2,762,272, 2,860,097 and 3,616,385 incorporated herein by reference.

Generally, for stability of the membranes it is necessary to employ temperatures below about 70° C. during electrodialysis. While in terms of overall efficiency, it is preferred to carry out the electrodialysis step at about the temperature within the reaction stage serve by each electrodialysis unit e.g., from about 15° to about 50° C. with temperatures from about 40° to 50° C. being preferred. As will be apparent to those skilled in the art, the temperature of the reaction step can be suitably controlled by adjusting the temperature of the recirculating concentrate stream to remove at least part of the heat of reaction resulting from the formation of the dichlorohydrin.

The diluate stream, after electrodialysis is depleted in chloride and hydrogen ions and is recycled back to reaction zone, and in a multistage reaction zone to the same reaction stage.

The present process is readily adapted to a single stage reaction zone. It is also readily adapted to dichlorohydrin process comprising a number, for example three to five reaction stages in series flow. The process may be readily adpated to such multistage process by installing a separate electrodialysis zone to electrodialyse the reaction mixture from each stage, or to electrodialyze the reaction mixture of just one stage, e.g., the first stage or of any subsequent stage. Preferably, in a three stage reaction system the reaction mixture of at least the second stage is electrodialyzed.

The concentrate stream from each electrodialysis zone may be handled separately, or maybe combined with the concentrate stream from one or more additional electrodialysis zones, and hydrogen ions in the combined stream are substantially neutralized with a basic substance. Preferably, at least 60% of the hydrogen ions in the concentrate stream are neutralized, more preferably at least 75% are neutralized. Although in principal, any basic acting substance can be employed to neutralized the hydrochloric acid in the concentrate stream, preferred materials are the hydroxides, carbonates and bicarbonates of Group I or Group II metals such as lithium, potassium, sodium, and calcium and magnesium. For Group II metals the oxides may also be suitably employed, such as e.g., calcium oxide and magnesium oxide. Based upon low cost and ready availability the use of sodium hydroxide, calcium oxide, calcium hydroxide and calcium carbonate, especially in commonly available forms such a caustic soda, lime and limestone are particularly preferred. During operation of the process a relatively small volume the concentrate stream is withdrawn for subsequent treatment or disposal. Typically, this will amount to from about 5–15% volume of the flow rate of the reaction zone throughput.

Reference is made to the FIGURE which represents a schematic flow of a preferred embodiment of the invention wherein a portion of the reaction mixture from each reaction stage is electrodialyzed to improve the overall efficiency of the dichlorohydrin production process. The FIGURE does not purport to show conventional pumps, instrumentation and valving present in a typical process.

Feed water is introduced via line 10 into the first reaction stage 12 of a reaction zone comprised of three stages. As will be apparent to those skilled in the art, the reaction zone may comprise three, four, five or more reaction stages, as desired however, use of more than five stages adds considerably to the cost of the facility with small additional improvement. Allyl chloride is introduced into said first reaction stage 12 via line 14 and chlorine is added in substantially equimolar amount via line 16. Although the reaction stages may comprise a stirred or agitated vessel, preferably each stage is a circulating loop reactor as shown and as described in greater particularily e.g., in U.S. Pat. No. 2,714,121; each stage preferably is sized to permit circulation of the reaction components at a rate at least 250 and up to about 400 times the volume of allyl chloride added to each reaction stage. A portion of the reaction mixture is continuously passed via line 18 to first electrodialysis zone 20. The amount of each stage reaction mixture passed to the corresponding electrodialysis zone may vary considerably, depending upon the reaction temperature, membrane area and particular electrodialysis conditions e.g., the particular membrane, applied voltage etc, but will generally be in the volume ratio range from about 0.5 to 20, normally 1 to 10 and particularly from about 2 to about 6 volumes of fresh feed throughput per reaction stage. The first stage reaction mixture having a temperature of e.g., 40° C.–55° C. and containing about 0.28 molar dichlorohydrin and 0.07N hydrochloric acid is fed to the first electrodialysis zone 20 comprised of alternating anionic exchange membranes designated at 203 QZL-386 and cationic exchange membranes designated as 61 CZL-386 which membranes are avialable from Ionics, Inc., Watertown, Mass. In general, the voltage across each stack of membrane is arranged so that there is a voltage of about 0.5 to about 3.0 volts per cell pair, with a voltage of about 1.0 to 2.5 being preferred. The ions are removed into a concentrate stream which contains a basic material such as lime slurry added via line 36 to the concentrate stream inlet line 34. Generally the basic material is added in sufficient amount so as to neutralize a substantial amount of the hydrogen ions in effluent from said first electrodialysis zone 20 by maintaining pH in the range from above about 2 and typically from about 5.0 to about 6.5. From said first electrodialysis zone a dilute stream comprising about 0.28M dichlorohydrin and 0.01N HCl is returned via line 40 to first reaction stage 12. A portion of the first stage reaction mixture is passed via line 42 to second reaction stage 44. Allyl chloride is continuously fed via line 46, and a substantially equimolar amount of chlorine is fed via line 48 into the circulating aqueous reaction mixture of the second stage. A portion of the said second stage reaction mixture containing about 0.53M, dichlorohydrin and about 0.07N HCl is continuously diverted via line 50 to second electrodialysis zone 52.

The conditions in the second electrodialysis zone are substantially like those in the first electrodialysis zone resulting in removal of ions into the concentrate stream entering the second electrodialysis zone via line 24 and leaving via line 26, and wherein they are neutralized with base previously added via line 36, and/or optionally via line 37. The dilute stream containing about 0.01N hydrochlorlic acid is passed via conduit 54 to second reaction stage 44. In a like manner portion of the circulating second reaction stage reaction mixture is diverted via line 56 to the third reaction stage 58 wherein allyl chloride is continuously added via line 60 and a substantially equimolar amount of chlorine is added via line 62. A portion of the third stage reaction mixture is continuously diverted via line 64 to third electrodialysis zone 66 operated as substantially the conditions of the two previous electrodialysis zones and the diluate stream is returned to said third reaction zone stage via line 68 as to maintain an average hydrochloric acid concentration of about 0.07N hydrochloric acid in said third stage. Ions removed in the third electrodialysis zone 66 are passed into the concentrate stream entering via line 28 and exiting via line 30 where they are neutralized with base added via line 36, or optionally via line 37 and/or line 38.

In a preferred embodiment, the concentrate stream from all the electrodialysis zones are combined for neutralization and recirculation as shown, and, in a particularly preferred embodiment the recirculated concentrate stream is cooled via chiller 33 and passed via lines 35 and 34 to the first electrodialysis zone 20. By use of the chiller on the concentrate lines, some of the heat generated in the reaction zone may be removed from the feed to the eltcrodialysis zone during electrodialysis. A relatively small volume of the circulating neutralized concentrate is continuously withdrawn via line 31 for treatment or disposal. Make-up concentrate volume, when required, is obtained by the addition of more aqueous base solution, or by the addition of a small amount of make-up water (not shown). Generally the combined concentrate stream may be operated with a concentration up to about the solubility limit of the components therein, but preferably at a concentration up to about 4N of the chloride of the basic material added.

EXAMPLE

To demonstrate the difference in required membrane area required according to the invention, compared to without neutralization of the concentrate, several experiments were conducted with a commerically available packaged electrodialysis unit available under the trade name "Stackpack" from Ionics, Inc. cation exchange membranes 61 CZL-386 and anion exchange membranes 203 QZL-356, available from Ionics, Inc. were used. The feed which contained a synthetic dichlorohydrin reaction mixture containing 0.5%w and 1.2%w organics and 0.1N chloride was electrodialyzed at 25° C. to produce a diluate containing 0.01N chloride. The concentrate stream which was continuously neutralized with a concentrated sodium hydroxide solution to maintain a pH above about 2, i.e., a pH in the range from 2 to 3. Results are shown in the following table.

TABLE

EFFECT OF CONCENTRATE STREAM NEUTRALIZATION ON THE EFFICIENCY OF ELECTRODIALYSIS SYNTHETIC DICHLOROHYDRIN REACTION
Conditions: Diluate concentration reduced from 0.1N Cl$^-$ to 0.01N at 25° C.

| | | Organics | | | | Effective Cell Pair Area ft/lb HCl-hr | |
|---|---|---|---|---|---|---|---|
| Run | Cl in Concentrate N | Diluate % w | Concentrate % w | V/cp | Current Efficiency min | Power Consumption Kwh/lb HCl | With Neutralization | Without[a] Neutralization |
| 1 | 0.4 → 0.5 | 0.5 | 1.5 | 1.5 | 86 | 0.514 | 7.3 | 14.6 |
| 2 | 0.2 → 0.3 | 1.2 | 1.5 | 1.5 | 94.6 | 0.459 | 6.9 | 12.75 |
| 3 | 0.2 → 0.3 | 1.2 | 1.5 | 1.5 | 93.6 | 0.484 | 7.4 | 12.33 |
| 4 | 0.2 → 0.3 | — | — | 2.2 | 80 | 0.815 | 6.4 | 7.17 |
| 5 | 0.2 → 0.3 | — | — | 1.5 | 90.6 | 0.456 | 6 | 11.93 |

[a]Effective Cellpair Areas (ECPA) required for the same electrodialytic separation but without neutralization were calculated to correspond to those required at the power consumption obtained in the experimental runs with neutralization, with about 0.5 volts per cell pair (V/cp).

In the table, in the column without neutralization of the concentrate, data are calculated at the same power consumption per pound of hydrogen chloride electromigrated as those with neutralization, and based upon experimentally determined more optimal voltage for electrodialysis of the acid of 0.5 volts per cell pair. As shown in the table, the effective cell pair membrane area (ECPA) needed with neutralization of the concentrate is substantially lower than that needed when no neutralization of the concentrate is applied. It has been found that neutralization of the reaction mixture before electrodialysis does not offer a significant advantage over no neutralization, particularly where the concentration gradient of chloride ion between the diluate and concentrate streams is in the range below about 0.2 normal.

What is claimed is:

1. In a continuous process for the production of an aqueous solution of dichlorohydrin by the reaction of allyl chloride, water and chlorine in a reaction zone, the method for removing by-product chloride and hydrogen ions which comprises:
（a) electrodialyzing a significant part of the reaction mixture in an electrodialysis zone to afford (1) a concentrate stream having a chloride content higher than that concentrate inlet feed to said electrodialysis zone, and (2) a diluate stream containing dichlorohydrin and having a lower chloride content than said reaction mixture electrodialysis feed,
(b) neutralizing a substantial portion of the hydrogen ions in the concentrate stream by the addition of a basic substance,
(c) withdrawing a portion of said neutralized concentrate stream, and
(d) recycling said diluate stream from said electrodialysis zone to said reaction zone.

2. A process as in claim 1 wherein step (b) at least about 60% of the hydrogen ions in the concentrate stream are neutralized.

3. A process as in claim 1 wherein step (b) the same basic substance is selected from caustic soda, lime and limestone.

4. A process as in claim 1 wherein the reaction zone comprises at least three reaction stages arranged in series flow.

5. A process as in claim 4 wherein the reaction zone comprises three to five reaction stages arranged in series flow.

6. A process as in claim 4 wherein the reaction mixture of the second stage is electrodialyzed.

* * * * *